United States Patent [19]
Nacamuli et al.

[11] Patent Number: 6,051,744
[45] Date of Patent: *Apr. 18, 2000

[54] LOW PRESSURE HYDRODEALKYLATION OF ETHYLBENZENE AND XYLENE ISOMERIZATION

[75] Inventors: Gerald J. Nacamuli, Mill Valley; Charles R. Wilson, San Francisco; Roger F. Vogel, Fairfield, all of Calif.

[73] Assignee: Chevron Chemical Company LLC, San Francisco, Calif.

[ * ] Notice: This patent is subject to a terminal disclaimer.

[21] Appl. No.: 09/213,839

[22] Filed: Dec. 17, 1998

[51] Int. Cl.⁷ .................. C07C 5/22; C07C 4/12; C01G 35/06
[52] U.S. Cl. .................. 585/481; 585/482; 585/489; 208/138
[58] Field of Search .................. 585/481, 485, 585/484; 208/138

[56] References Cited

U.S. PATENT DOCUMENTS

| | | | |
|---|---|---|---|
| Re. 31,782 | 12/1984 | Olson et al. | 585/481 |
| 3,856,872 | 12/1974 | Morrison | 260/668 |
| 4,098,836 | 7/1978 | Dywer | 260/668 A |
| 4,152,363 | 5/1979 | Tabak et al. | 585/481 |
| 4,158,676 | 6/1979 | Smith et al. | 585/481 |
| 4,159,283 | 6/1979 | Nicoletti et al. | 585/481 |
| 4,163,028 | 7/1979 | Tabak et al. | 585/481 |
| 4,188,282 | 2/1980 | Tabak et al. | 208/134 |
| 4,218,573 | 8/1980 | Tabak et al. | 585/481 |
| 4,236,996 | 12/1980 | Tabak et al. | 208/134 |
| 4,300,014 | 11/1981 | Yamasaki et al. | 585/481 |
| 4,331,822 | 5/1982 | Onodera et al. | 585/482 |
| 4,351,979 | 9/1982 | Chester et al. | 585/481 |
| 4,385,195 | 5/1983 | Butter et al. | 585/481 |
| 4,482,773 | 11/1984 | Chu et al. | 585/481 |
| 4,485,185 | 11/1984 | Onodera et al. | 502/71 |
| 4,700,012 | 10/1987 | Onodera et al. | 585/481 |
| 4,873,387 | 10/1989 | Sachtler et al. | 585/482 |
| 4,899,011 | 2/1990 | Chu et al. | 585/481 |
| 4,939,110 | 7/1990 | Sachtler et al. | 502/66 |
| 5,877,374 | 3/1999 | Nacamuli et al. | 585/489 |

FOREIGN PATENT DOCUMENTS 499 799 A1  1/1992  European Pat. Off. .

Primary Examiner—Walter D. Griffin
Assistant Examiner—Thuan D. Dang
Attorney, Agent, or Firm—D. M. Tuck

[57] ABSTRACT

A new process for the hydrodealkylation of ethylbenzene and the isomerization of xylenes at low pressure and at a low hydrogen to ethylbenzene mole ratio as well as a low hydrogen to hydrocarbon feed mole ratio using a catalyst comprising (a) HZSM-5 having a particle size less than 1.0 microns, and (b) a Group VIII metal such as platinum.

17 Claims, 2 Drawing Sheets

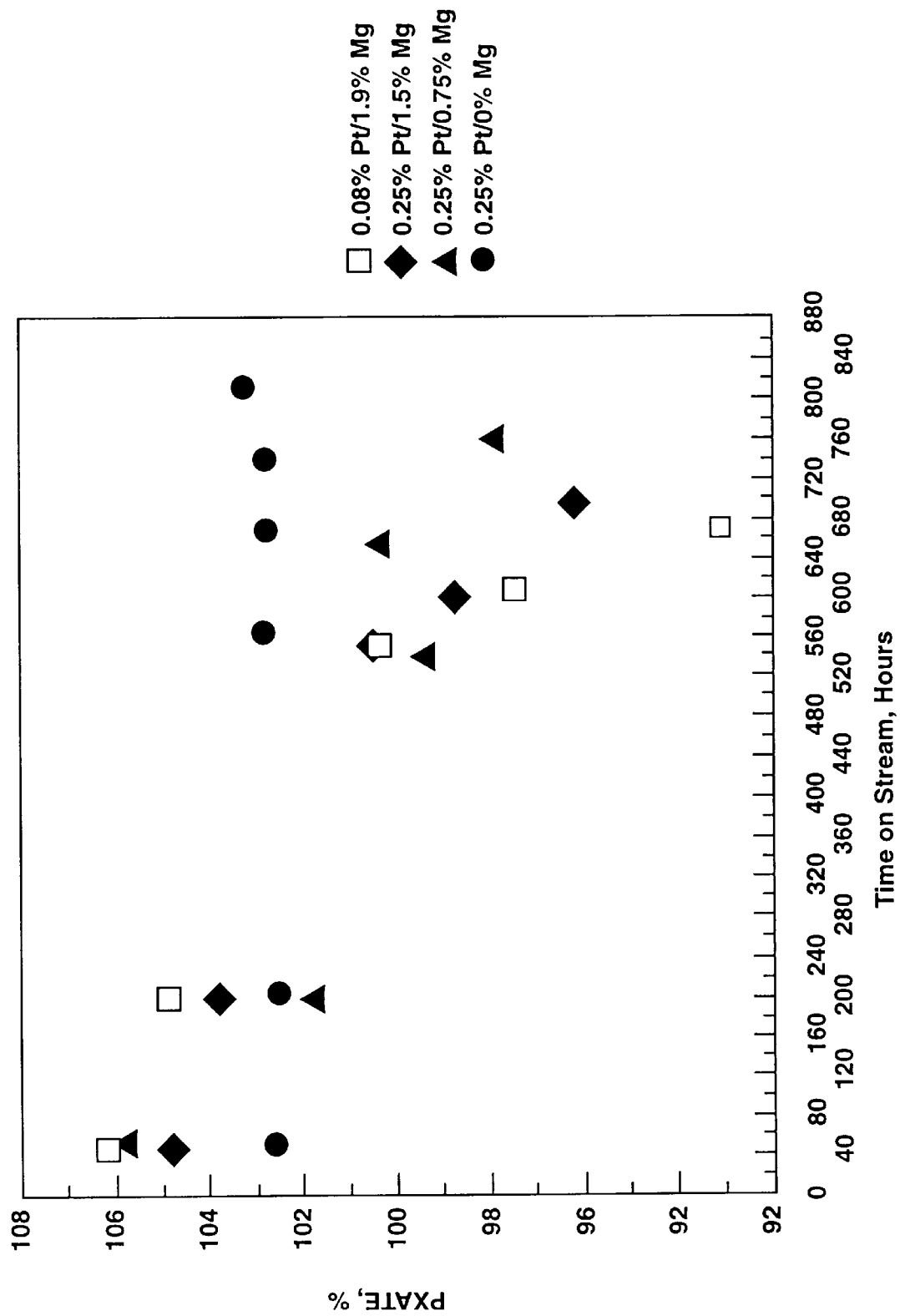

LOW PRESSURE HYDRODEALKYLATION OF ETHYLBENZENE AND XYLENE ISOMERIZATION

FIELD OF THE INVENTION

The present invention relates to a catalyst and process for hydrodealkylating ethylbenzene and isomerizing xylenes. Preferably, the ethylbenzene and xylenes are in a $C_8$ aromatics stream lean in paraxylene.

BACKGROUND OF THE INVENTION

The xylene isomers metaxylene, orthoxylene and, in particular, paraxylene, are important chemical intermediates. Orthoxylene is oxidized to make phthalic anhydride which is used to make phthalate based plasticizers among other things. Metaxylene is oxidized to make isophthalic acid which is used in unsaturated polyester resins.

However, paraxylene has by far the largest market of the three isomers. The largest use of paraxylene is in its oxidation to make terephthalic acid. Terephthalic acid in turn is used to make polymers such as polytrimethyleneterephthalate, polybutyleneterephthalate (PBT), and polyethyleneterephthalate (PET). PET is made via condensation polymerization of terephthalic acid with ethylene glycol.

PET is one of the largest volume polymers in the world. It is used to make PET plastics (e.g., two liter PET bottles). It is also used to make polyester fiber which, in turn, is used to make clothes and other fabrics. Polyester fiber is used both as a homofiber, as well as a blended fiber, such as a blend with cotton. Given the large market for PET plastics and fibers, there is a substantial demand for high purity paraxylene. The demand for paraxylene is several times larger than the demand for ortho and metaxylene. The demand for paraxylene is also larger than the amount of paraxylene in the xylenes recovered as a by-product, such as the xylenes recovered from reformate (from catalytic reformers) and from pygas (from high temperature cracking to make light olefins).

Because the demand for paraxylene is so much larger than the demand for the other xylene isomers and is larger even than the supply of paraxylene in xylenes recovered as a by-product, it has been found that isomerization of xylene isomers is desirable to increase the amount of paraxylene production. Paraxylene is typically produced by reforming or aromatizing a wide boiling range naphtha in a reformer, for example, a CCR (Continuous Catalytic Reformer), and then separating by distillation a $C_8$ aromatics rich fraction from the reformer effluent. This $C_8$ fraction comprises near equilibrium amounts of ethylbenzene and the three xylene isomers, namely, para-, meta- and ortho-xylene. The paraxylene in this $C_8$ aromatics fraction is separated by either crystallization or adsorption. Rather than simply returning the paraxylene depleted $C_8$ aromatics stream to the refinery for a relatively low value use such as gasoline blending, the $C_8$ aromatics stream which is depleted in paraxylene is typically further processed by passing it over a xylene isomerization catalyst in a xylenes isomerization unit. The resulting $C_8$ aromatics stream, which now has an approximately equilibrium concentration of xylenes, i.e., a higher concentration of paraxylene, is recycled to the paraxylene separation process.

The xylene isomerization unit typically serves at least two functions. First, it re-equilibrates the xylenes portion of the stream. Thus, in effect, it is creating paraxylene from the other xylene isomers. Second, it transalkylates or hydrodealkylates the ethylbenzene to facilitate its removal from the $C_8$ aromatics fraction. Since ethylbenzene boils in the same range as the xylene isomers, it is not economic to recover/remove the ethylbenzene by distillation, hence it is included in the $C_8$ aromatics fraction that is fed to the paraxylene separation process. Ethylbenzene is in general an inert from a para-xylene production standpoint, except for those para-xylene production complexes which utilize a xylene isomerization process where the ethylbenzene is converted to xylenes. However, as pointed out earlier, such a process is limited in its ethylbenzene conversion by $C_8$ aromatics equilibrium. Therefore, for those cases where ethylbenzene is an inert, it is highly desirable to remove as much ethylbenzene as possible per pass so that it does not accumulate in the recycle loop. If that were to occur, a bleed stream out of the para-xylene production loop would be necessary which would reduce para-xylene production. Thus, a critical function of the isomerization plant is to react-out the ethylbenzene by either hydrodealkylation or transalkylation/disproportionation depending on the type of isomerization process.

Current xylene isomerization technology is based on two types of processes, high pressure processes and a low pressure process. Furthermore, within the high pressure processes, there are two types of such processes. U.S. Pat. No. 4,482,773 and U.S. Pat. No. 4,899,011 are two references dealing with one type of the high pressure process, usually carried out at 150 psig and higher and in the presence of hydrogen. U.S. Pat. No. 4,584,423 is a reference dealing with low pressure isomerization, usually carried out at less than 150 psig, for example, between about 25 and 100 psig and in the absence of hydrogen.

In the '773 and '011 high pressure processes, a $C_8$ aromatics-rich hydrocarbon feed is contacted with a catalyst containing a ZSM-5 zeolite. Xylene isomerization is carried out simultaneously with ethylbenzene hydrodealkylation to benzene and ethane. The hydrogen/hydrocarbon feed mole ratio is between 2/1 and 4/1. In both these patents, the objective is to achieve high levels of ethylbenzene conversion to isomerize the xylene to achieve a higher content of paraxylene, preferably an equilibrium content of paraxylene and to have low xylene losses. In the '773 process, ethylbenzene conversion levels are about 60% and xylene losses are about 2% yielding an ethylbenzene conversion/xylene loss ratio of about 30/1. Similar values are achieved with the '011 high pressure process, but at ethylbenzene conversions of about 70%. For both these high pressure processes, the catalyst system is very xylene selective.

In U.S. Pat. No. 4,482,773, the catalyst used comprises platinum and magnesium on a ZSM-5 zeolite. The preferred catalyst is an HZSM-5 (H meaning that the ZSM-5 is predominately in the hydrogen form) with a preferred crystal size of 1–6 microns. The examples in U.S. Pat. No. 4,482,773 disclose a $H_2$/HC feed mole ratio of 2/1 or higher.

The high pressure process of U.S. Pat. No. 4,899,011 is similar to the '773 process but uses a dual catalyst bed system. The objective is to hydrodealkylate ethylbenzene in the first catalyst layer and complete the isomerization of xylenes in the second layer. The catalyst for both layers is a Pt containing ZSM-5, without any Group IIA metal such as Mg. The Pt ranges from 0.05–10 wt. %. The crystal size of the first layer is 1 micron minimum compared to 0.1 micron maximum for the second layer. In addition, the top layer is a more acidic ZSM-5 than the second layer. Operating conditions for the '011 process are 400–1000° F., 0–1000 psig, 0.5–100 WHSV, and a $H_2$/HC feed mole ratio of 0.5/1 to 10/1.

The catalysts for both U.S. Pat. No. 4,482,773 and U.S. Pat. No. 4,899,011 have good xylene isomerization activity as determined by the Paraxylene Approach To Equilibrium (PXAPE) which reaches values of 100–103%. A PXAPE of 100% indicates that the paraxylene concentration on a xylene basis is at equilibrium. The catalyst of both processes is based on ZSM-5. In the case of the '773 process, the catalyst contains Pt and possibly Mg. The catalyst has a silica/alumina ratio of about 50/1 to 100/1 and a crystal size of 1–6 microns. In the case of the '011 process, the catalyst bed consists of two catalyst layers, each of which contains Pt. Catalyst crystal size and acidity differ with the top catalyst having a crystal size of 2–4 microns and the bottom layer having a crystal size of 0.02–0.05 microns. In addition, as mentioned above, the top layer is more acidic than the bottom layer.

It should be noted that within the high pressure xylene isomerization process technology, there is a sub-type of process where the objective is to eliminate the ethylbenzene by converting the ethylbenzene to xylenes. However, high levels of ethylbenzene conversion as in the '773 and '011 patents are not achieved with this type of process, because the ethylbenzene concentration is limited by the equilibrium concentration on a $C_8$ aromatics basis.

In addition to U.S. Pat. No. 4,899,011 and U.S. Pat. No. 4,482,773 discussed above, two other patents of interest are U.S. Pat. No. 4,467,129, issued Aug. 21, 1984 to Iwayama et al., and U.S. Pat. No. 4,899,010, issued Feb. 6, 1990 to Amelse et al.

U.S. Pat. No. 4,467,129 is very similar to the '733 and '011 processes, in that ethylbenzene is converted by hydrodealkylation and uses a mixture of mordenite and a ZSM-5 which contains rhenium. A ZSM-5 containing Mg and Re is disclosed. Platinum is not a catalyst component. The process operates at 572–1112° F., a pressure of 0–1370 psig, and a $H_2$/HC feed mole ratio of 1–50/1. The examples show a temperature of ~700° F., a pressure of 165 psig, and a $H_2$/HC feed mole ratio of 4/1. We estimate the WHSV at 3.5.

U.S. Pat. No. 4,899,010 is also an ethylbenzene hydrodealkylation/xylene isomerization process. It is based on the hydrogen form of a borosilicate equivalent of ZSM-5 known as AMS-1B. The catalyst contains 0.1–1.0 wt. % Pt. Operating conditions are 700–1000° F., 0–100 psig, and a $H_2$/HC feed mole ratio of 0.25–5.0. Ethylbenzene conversions are about 25–28% and the ethylbenzene conversion/xylene loss ratio is about 29.

Other patents of interest are U.S. Pat. Nos. 3,856,872; 4,098,836; and 4,152,263 which are discussed below.

U.S. Pat. No. 3,856,872 to Morrison utilizes a ZSM-5 catalyst containing a Group VIII metal, preferably nickel. Morrison operates at high pressure (150 to 300 psig) and a high hydrogen to hydrocarbon ratio of 6.5.

U.S. Pat. No. 4,098,836 to Dwyer provides an improved catalyst for xylenes isomerization comprising a zeolite such as ZSM-5 in combination with a group VIII metal present in minimum amount of 2.0 percent by weight of said zeolite. The group VIII metals exemplified are nickel, iron, and/or cobalt. Possible operating conditions disclosed by Dwyer include a hydrogen to hydrocarbon ($H_2$ to HC) mole ratio of from about 0.1 to about 100 and a pressure of from about 50 psig to about 500 psig. Examples in the patent are limited to a $H_2$ to HC mole ratio of 1 and pressures of about 200 psig (pressures given in the examples range from 183 to 214 psig).

U.S. Pat. No. 4,152,363 to Tabak and Morrison is another xylenes isomerization patent which discloses a catalyst that can comprise a ZSM-5 zeolite and a group VIII metal. '363 teaches operating conditions which comprise a pressure from about 20 to about 500 psig and a $H_2$ to HC mole ratio of about 1 to 10.

In the low pressure xylene isomerization process, which operates without any hydrogen present, ethylbenzene conversion is achieved by the disproportionation of ethylbenzene. The products of this disproportionation reaction are benzene and di-ethylbenzene, a $C_{10}$ aromatic. Ethylbenzene (EB) is also converted by another reaction, namely, by transalkylation with the xylenes. This latter reaction produces benzene and di-methyl-ethylbenzene, also a $C_{10}$ aromatic. This reaction with xylenes results in an undesirable loss of xylenes. Another reaction mechanism which contributes to xylene loss is the disproportionation of xylenes to produce toluene and trimethylbenzenes, a $C_9$ aromatic. All these reactions are a function of the catalyst acidity. Operating conditions are such as to achieve ethylbenzene conversions of about 25–40%. However, the xylene losses are high, on the order of 2.5–4.0%, resulting in an ethylbenzene conversion/xylene loss ratio of 10/1. Thus, at 40% ethylbenzene conversion, the xylene losses are 4%. Furthermore, high levels of ethylbenzene conversion, in the range of 50–70% are not practical as the temperature required to achieve these levels of ethylbenzene conversion would be quite high. At 70% ethylbenzene conversion, the temperature required is about 60–70° F. higher than that required to achieve 50% ethylbenzene conversion. In addition, the coking rate would also be substantially higher due to the higher operating temperature and higher level of ethylbenzene conversion. The net effect of operating at higher ethylbenzene conversion is a substantial reduction in the catalyst life.

One key goal of xylene isomerization catalyst development efforts has been to reduce xylene losses at constant ethylbenzene conversion, or to achieve higher ethylbenzene conversions while reducing the xylene losses.

U.S. Pat. No. 4,584,423, which describes a low pressure isomerization process, discloses that a Mg/ZSM-5 extrudate resulted in a 40% reduction in xylene loss when used in low pressure isomerization, and a Zn/ZSM-5 extrudate resulted in a 30% reduction in xylene loss when used in low pressure isomerization operating at 25% ethylbenzene conversion. However, the operating temperature for the reaction zone was higher relative to the base case using ZSM-5 catalyst. Operation to achieve 50% ethylbenzene conversion would have required even higher operating temperatures.

From a catalyst stability standpoint, the high pressure processes which operate in the presence of hydrogen have catalyst systems which are an order of magnitude more stable than the low pressure process which operates in the absence of hydrogen. For high pressure processes, catalyst stability is believed enhanced by using a catalyst which contains a hydrogenation/dehydrogenation metal component, such as for example platinum, palladium, or nickel, and by using a high hydrogen partial pressure. The high hydrogen partial pressure is achieved by combining a high system/process pressure with a high hydrogen/hydrocarbon feed mole ratio, for example, 4/1. This is equivalent to a hydrogen concentration of approximately 80 mole %.

Accordingly, in a low pressure process, it would be desirable to achieve the performance parameters of the high pressure isomerization processes and achieve high levels of ethylbenzene conversion, while simultaneously achieving xylene isomerization and very low xylene losses, and achieving high stability for the catalyst.

SUMMARY OF THE INVENTION

According to the present invention, a process is provided for hydrodealkylation of ethylbenzene and isomerization of xylenes. The process comprises contacting, in a reaction zone, a hydrocarbon feed containing ethylbenzene and xylenes, with a catalyst comprising ZSM-5, a Group VIII metal; and wherein the paraxylene content of the xylenes in the feed is less than an equilibrium amount, the contacting is carried out in the presence of gaseous hydrogen, and the ZSM-5 has a crystal size of between 0.2 and 0.9 microns; to thereby hydrodealkylate ethylbenzene to produce benzene and isomerize xylenes to produce paraxylene.

Preferred reaction conditions, in the reaction zone of the present invention, include a temperature of 500° F. to 1000° F., more preferably 600° F. to 900° F., and still more preferably 700° F. to 900° F.

The reaction zone pressure is below 200 psig, preferably 0 to 150 psig, more preferably below 125 psig, and still more preferably below 90 psig for example, 25 to 90 psig. Particularly preferred pressure is 10 to 80 psig for the reaction zone of the present invention. An advantage of the present invention is achievement of high ethylbenzene conversion, excellent xylene isomerization and surprisingly low xylene losses at low pressure. A further advantage of the present invention is that the catalyst exhibits high xylene isomerization activity as evidenced by an initial Paraxylene Approach To Equilibrium (PXATE) of 100+%, as well as high xylene isomerization stability. This latter key catalyst quality is evidenced by a very minor decline in the PXATE with time. This stability of the PXATE allows for long and useful catalyst life.

According to an alternate embodiment of the present invention, a particularly preferred low pressure in the reaction zone is below 40 psig, and a still more preferred pressure is below 35 psig.

The weight hourly space velocity based on the zeolite (WHSVZ), preferably is 2 to 20, more preferably 3 to 15, still more preferably 4 to 10, and most preferably 6 to 8.

Preferably, the feed to the reaction zone is a hydrocarbon stream comprising mainly $C_8$ hydrocarbons, containing ethylbenzene, and a mixture of xylenes that is below equilibrium in paraxylene content. The hydrogen to ethylbenzene mole ratio in the feed is 0.3 to 15, preferably 0.7 to 15, and more preferably 1.0 to 11. Particularly preferred hydrogen to ethylbenzene mole ratios are between 1.0 and 7.0, and most preferably between 1.0 and 3.0 for the feed to the reaction zone of the present invention.

The Group VIII metal of the catalyst used in the reaction zone of the process of the present invention preferably is platinum. Preferably, the ZSM-5 component used to make the catalyst is predominantly in the hydrogen form.

Among other factors, the present invention is based on our finding that when combining use of:

(a) a ZSM-5 based catalyst having a small ZSM-5 crystal size less than 0.9 microns, and associated with a Group VIII metal such as platinum with (b) low pressure, and (c) reaction conditions including the presence of low concentrations of gaseous hydrogen, a surprisingly high ethylbenzene conversion is achieved in the reaction zone, while also achieving low xylene losses and excellent xylene isomerization activity, i.e. the ability of the catalyst to isomerize the xylenes.

Surprisingly, we have also found that excellent xylene isomerization activity, as evidenced by a PXATE of 100+%, and excellent xylene isomerization stability as evidenced by a minor decline in the PXATE with time, can be maintained with the catalyst of the present invention when operating at low pressure and with a low hydrogen to EB mole ratio and while achieving high EB conversion at surprisingly low xylene losses.

While others have sought to achieve similar results by the addition of various metals and in particular alkaline earth metals, or by various catalyst treatments, such as sulfiding, no such additives or treatments are needed for the catalyst of the invention. Thus a further advantage of the catalyst of the invention is that the manufacture of the catalyst is substantially simplified resulting in a lower manufacturing cost.

Further, we have found that due to the relatively small amount of hydrogen needed to facilitate the hydrodealkylation reaction in the process of the present invention, in accordance with a preferred embodiment of the present invention, recycle of unused hydrogen to the reaction zone is not required. Not having to recycle hydrogen simplifies the process and allows the process to be performed with less equipment and a lower cost of operation. In particular, according to preferred embodiments, this invention eliminates the requirement for a recycle compressor in the process.

Also, the present invention allows the use of relatively low pressure in the reaction zone. Accordingly, the reactors and associated piping and equipment do not have to be built to withstand high pressures required when using prior art processes.

Another advantage we have found resulting from the present invention is that the low pressure isomerization process, which in the past could not utilize the hydrodealkylation type process for the removal of ethylbenzene from the $C_8$ aromatics and paraffins stream, can now be retrofitted to take advantage of this more efficient process. Such older low pressure isomerization plants, still in use today, were built to operate at relatively low pressures and without hydrogen. They could not be economically retrofitted to accommodate prior art hydrodealkylation processes, as these require high pressures in excess of 150 psig, as well as large volumes of hydrogen and the ability to recycle the hydrogen.

Still another advantage of the present invention is that, in accordance with a preferred embodiment, effective removal of a portion of the $C_8$ paraffins present in the feed to the hydrodealkylation/isomerization reaction zone is achieved by hydrocracking such paraffins to lighter paraffins, which lighter paraffins are easily removed from the $C_8$ aromatics. Preferably, at least 15%, more preferably at least 20% of the $C_8$ paraffins are effectively removed in this manner. This is of particular advantage in paraxylene production processes that utilize a feed comprising unextracted, predominately $C_8$ hydrocarbons feed containing both aromatics and nonaromatics (paraffins) from a high octane catalytic reformer. Such unextracted reformate can include several percent nonaromatics. These nonaromatics may build up in the paraxylene processing loop requiring a bleed stream to control their concentration, unless conversion is achieved in the xylene isomerization step.

Still a further advantage of the present invention is that it minimizes the system pressure and the amount of hydrogen, expressed in terms of the hydrogen to ethylbenzene mole ratio, needed for the hydrodealkylation reaction. Hydrogen is a valuable and expensive commodity in a refinery or chemical complex. In the present invention, minimal hydrogen is required. In addition, the hydrogen required preferably is used at a relatively low pressure, allowing the hydrogen from another higher pressure unit [such as from a conventional reformer using a bifunctional (acidic) reforming catalyst, or AROMAX® type reformer using a monofunctional (nonacidic) type catalyst] to be used in a "stepped" arrangement. Such a "stepped" arrangement adds to the cost savings benefits of this invention.

Preferred Group VIII hydrogenation metal components for the catalyst used in the process of the present invention include platinum, palladium, and nickel. Platinum is particularly preferred as the hydrogenation metal in the catalyst used in the present invention. Preferably, the amount of hydrogenation metal is between 0.05 and 20 wt. %, more preferably between 0.05 and 10 wt. %, and still more preferably between 0.075 and 8, based on the weight of zeolite in the catalyst. For the particularly preferred hydrogenation metal platinum, the most preferred range is 0.075 to 0.5 wt. %.

We have found that the predominantly hydrogen form of the ZSM-5 and the careful control of the silica to alumina ratio in the catalyst are particularly advantageous in achieving a moderated acidity and pore constraint catalyst for use in the process of the present invention.

DETAILED DESCRIPTION OF THE INVENTION

According to the present invention, a catalyst and process are provided for achieving high levels of ethylbenzene conversion, xylene isomerization and low xylene losses.

The present invention is particularly useful in a commercial scale ethylbenzene hydrodealkylation/xylene isomerization process. Such a process is often referred to simply as a xylenes isomerization process. For the purposes of this invention a commercial scale process for the hydrodealkylation of ethylbenzene and the isomerization of xylenes has a hydrocarbon feed rate of at least 100 bbls per day, preferably at least 500 bbls per day, and more preferably at least 1000 bbls per day.

Preferably, the catalyst comprises a small crystal size ZSM-5 containing a Group VIII metal (e.g., platinum). Preferred small crystal size ZSM-5 of the catalyst used in the present invention is discussed herein below, as is preferred silica to alumina ratio.

In a particularly preferred catalyst, the Pt content is 0.075 to 0.5 wt. %.

In accordance with the present invention, the process is operated at low pressure, and preferably with a low flow of hydrogen. The low flow of hydrogen may be referred to as "trickle flow". Preferably, the trickle flow is once-through, that is, with no recycle hydrogen.

Ethylbenzene is converted by hydrodealkylation, preferably to benzene and ethane. This is in contrast to prior art low pressure processes where the EB is converted by disproportionation which is accompanied by high xylene losses and formation of substantial amounts of heavy material such as C9 aromatics and heavier.

The xylene losses in accordance with the process provided by the present invention are substantially reduced relative to prior low pressure processes. Also, in the process of the present invention, a high degree of xylene isomerization to paraxylene is achieved.

In the process of the invention, the xylenes in the feed, which contain paraxylene on a xylene basis in an amount which is less than that at thermal equilibrium on a xylene basis, are converted (or isomerized) such that in the effluent from the isomerization reaction zone, the paraxylene content on a xylene basis preferably is at least at 90% of the thermal equilibrium content (or concentration). More preferably, in the present invention, the xylenes in the feed are converted such that in the effluent from the isomerization reaction zone, the paraxylene content on a xylene basis is at least at 95% of the thermal equilibrium content (or concentration). Still more preferably, in the present invention, the xylenes in the feed are converted such that in the effluent from the isomerization reaction zone, the paraxylene content on a xylene basis is at least at 100% of the thermal equilibrium content (or concentration).

Within the parameters of the present invention with a trickle flow of hydrogen at low pressure, an EB conversion fouling rate of the catalyst is achieved that is preferably less than 1 degree F. per day, and more preferably less than 0.5 degrees F. per day.

In addition, we have found that the preferred catalyst and process conditions described herein for the present invention achieve high catalyst stability from an EB conversion standpoint relative to prior low pressure processes. The catalyst of the invention allows operation at high/higher EB conversions than possible with prior art low pressure processes, while still achieving better catalyst stability than prior art low pressure processes. Note that by higher catalyst stability we mean lower catalyst aging rate resulting in a longer catalyst life. The preferred catalyst and process conditions of the invention also result in good initial xylene isomerization activity as demonstrated by a PXATE of 100+%. In addition, while the catalyst shows excellent stability from an EB conversion standpoint, the catalyst also shows excellent stability from a xylene isomerization standpoint. This xylene isomerization stability is demonstrated by a very slow decline in the PXATE with time. A slow decline in PXATE as described herein is advantageous because it allows the cycle time between catalyst regenerations to be increased and effectively decreases the overall aging rate of the catalyst.

As stated above, the present invention uses a catalyst comprising ZSM-5 aluminosilicate. Preferably, the ZSM-5 is in the hydrogen form. ZSM-5 can have most of the original cations associated therewith replaced by a wide variety of other cations according to techniques well known in the art. In a preferred embodiment of the present invention, most of the original cations are replaced by hydrogen by methods such as ammonium-exchange followed by calcination.

The crystal size of the ZSM-5 component of the catalyst used in the process of the present invention is less than 1.0 micron, preferably less than 0.9 microns, more preferably 0.2 to 0.9 microns, still more preferably 0.2 to 0.8 microns.

The silica/alumina ratio of the ZSM-5 of the catalyst used in the present invention is in the range of 10 to 300, preferably 30 to 200, more preferably from 30 to 150, still more preferably in the range of from 50 to 100, and most preferably is in the range of 70 to 90.

The preferred Group VIII hydrogenation metal for the catalyst used in the present invention is platinum (Pt). Preferably, the Pt content is from 0.05 to 1.0 wt. %, more preferably from 0.05 to 0.75, and still more preferably from 0.075 to 0.5 wt. %. Pt is believed to act as a hydrogenation/dehydrogenation component. Although not as preferred in the present invention, other Group VIII metals can be used such as palladium (Pd) or nickel (Ni). The Pt may be added by ion-exchange or by impregnation.

Palladium may be used as the Group VIII hydrogenation metal for the catalyst used in the present invention. Preferably, the Pd content is from 0.1 to 2.0 wt. %, more preferably from 0.1 to 1.5, and still more preferably from 0.15 to 1.0 wt. %.

Nickel also may be used as the Group VIII hydrogenation metal for the catalyst used in the present invention. Preferably, the Ni content is from 0.10 to 20 wt. %, more preferably from 0.1 to 10, and still more preferably from 1 to 8 wt. %.

Mixtures of Group VIII metals can also be used in conjunction with the ZSM-5 zeolite to produce a catalyst suitable for use in the present invention. Mixtures such as Pt and Ni; Pt and Pd; Pd and Ni; and Pt, Pd and Ni can be used in numerous different proportions in the present invention to achieve a suitable catalyst.

The catalyst preferably comprises zeolite bound with an inorganic matrix, such as alumina. A preferred form of the catalyst is bound zeolite extruded to a ¹⁄₁₆-in. diameter extrudate.

The feedstock for the process of the present invention is preferably obtained from a paraxylene separation process such as an adsorption process, a crystallization process, or a combination of both processes.

Such processes remove paraxylene from a $C_8$ boiling range feedstocks, leaving a paraxylene depleted stream. The paraxylene depleted stream contains a below equilibrium level of paraxylene, preferably 0–20% by weight paraxylene, more preferably 0–12% by weight paraxylene. Feeds that are obtained predominantly from an adsorption process will typically have lower amounts of paraxylene in the feed than a feed that is obtained from a paraxylene separation process based on crystallization.

According to a preferred embodiment, the process of the present invention comprises contacting the catalyst described herein with a $C_8$ aromatics stream which has a paraxylene concentration which is below equilibrium on a xylenes basis and which has an ethylbenzene concentration of 2–20 wt. %, preferably 5–20 wt. %, and a non-aromatic concentration of between 0 and 8 wt. %, preferably 0–5 wt. %.

In the process of the present invention, preferably, the hydrogen is added at a rate so that the mole ratio of hydrogen to ethylbenzene in the feed is preferably 1.0 to 7.0, and most preferably 1.0 to 3.0. The mole ratio of hydrogen to hydrocarbon in the feed is 0.02 to 1.0, preferably 0.04 to 1.0, more preferably 0.06 to 0.8, still more preferably 0.07 to 0.5, and most preferably 0.07 to 0.2.

In a preferred embodiment of the present invention, since the rate of hydrogen addition is so small—a trickle—relative to the feed, there is no need to recycle the unused hydrogen, thus the hydrogen is added on a once-through basis.

The temperature used in the reaction zone is preferably 500 to 1000° F., more preferably between 600 to 900° F.

Preferably, the reaction zone of the present invention is operated to achieve an ethylbenzene conversion of at least 20 wt. %, more preferably at least 35 wt. %, still more preferably at least 50 wt %, and most preferably 50 to 80 wt. %. The ethylbenzene conversion/xylene loss ratio of the present process is greater than 15/1, preferably greater than 20/1, and more preferably greater than 25/1.

Terms used in the art such as "lean in paraxylene" or "depleted in paraxylene" are generally used to indicate that a given stream contains less than an equilibrium amount of paraxylene relative to the other xylenes (metaxylene and orthoxylene). A stream that is lean in paraxylene or depleted in paraxylene is typical of a stream that has been subjected to a paraxylene separation process such as an adsorption or crystallization process in order to remove the paraxylene contained therein. Such a stream depleted in paraxylene is a typical feedstock to an isomerization type process of the present invention.

An important feature of the present invention is effective removal of a portion of the ethylbenzene from the $C_8$ feed by hydrodealkylation in the reaction zone. We have found that, in the process of the present invention, the hydrodealkylation can be accomplished with a surprisingly small amount of hydrogen at a surprisingly low pressure. As such, we have found that a useful measure for the present invention is hydrogen to ethylbenzene feed mole ratio, since the primary purpose of the hydrogen is to participate in the hydrodealkylation of the ethylbenzene. Stoichiometrically, one mole of hydrogen is required to hydrodealkylate one mole of ethylbenzene. Thus, the theoretical minimum amount of hydrogen required to hydrodealkylate 50% of the ethylbenzene in the feed is a hydrogen to ethylbenzene mole ratio of 0.5. In practice, more hydrogen is required since all of the hydrogen does not react and some of the hydrogen reacts with molecules other than ethylbenzene. For example, the hydrogen may be used in hydrogenating cracked paraffins in the reaction zone. Hydrogen may also saturate some of the aromatic rings.

The fouling rate of the catalyst used in the reaction zone is low under the process conditions of the present invention. Fouling of an isomerization catalyst is to a great extent caused by coke formation on the catalyst surface. Fouling of the catalyst decreases the performance of the catalyst. The decrease in performance, that is i.e. the loss in EB conversion, can be compensated for to a great extent by increasing the process temperature. The process temperature can only be increased so far, however. It is then necessary to regenerate the catalyst by removing the coke. If the time between required catalyst regenerations is too short for a given catalyst, due to a rapid fouling rate, the catalyst is not practical for a commercial unit. The rate of fouling of the catalyst is thus an important factor in the desirability of the catalyst.

The process of the invention may be carried out in a moving bed or fixed bed reactor. In a moving bed reactor and after reaching the end of a reaction cycle, the catalyst can be regenerated in a regeneration section/zone where the coke is burned off from the catalyst in an oxygen containing atmosphere such as air at a high temperature, after which the catalyst is recycled to the reaction zone for further contact with the feed. In a fixed bed reactor, regeneration can be carried out in a conventional manner by using initially an inert gas which contains a small amount of oxygen, e.g., 0.5 to 2.0%, to burn the coke off the catalyst in a controlled manner so as not to exceed a maximum temperature of 900° F. to 950° F.

The ZSM-5 zeolite component of the catalyst used in the process of the present invention can be prepared in various manners. Suitable preparation procedures are described in U.S. Pat. No. 3,702,886 to Argauer et al.

ZSM-5 embraces a family of crystalline aluminosilicates as set forth in more detail in U.S. Pat. No. 3,702,886, the disclosure of which patent is incorporated by reference into this specification.

The structure of the ZSM-5 class of zeolites is such that the pore sizes or apertures of the zeolite are in the intermediate size range of approximately 5 to 7 Angstroms, usually about 5.5 Angstroms. This is in contrast to the larger pore size zeolites, such as faujasite, or the smaller pore size zeolites such Linde Type A and erionite. The structure of ZSM-5 is described by Kokotailo et al. in *Nature,* Vol. 272, Mar. 30, 1978, page 437. The pore opening into the crystalline zeolite is delineated by the atomic structure. However, the pore opening or constraints may be modified by components added to the ZSM-5.

Although ZSM-5 is the preferred zeolite for use in the catalyst used in the process of the present invention, other zeolites of the ZSM-5 type are embraced within a broad embodiment of the present invention. These zeolites include ZSM-11, which is described in U.S. Pat. Nos. 3,709,979 and 4,108,881 (alternate synthesis), the disclosures of which are incorporated by reference into the present specification. Another publication that provides a synthesis of ZSM-11 is PCT publication WO9509812-A1 (also EP 721,427-A1).

According to an alternate embodiment of the present invention, besides ZSM-5, other intermediate pore zeolites having a pore size of approximately 5 to 7 Angstroms may also be used to form the catalyst used in the process of the present invention. ZSM-11 is included in such other intermediate pore size zeolites. However, the most preferred embodiment of the present invention uses ZSM-5 zeolite. ZSM-5 can be made in a variety of ways e.g. with and without seeding, with and without templates. One way of making ZSM-5 is exemplified below.

The ZSM-5 zeolite can be made by preparing a solution containing water, tetrapropyl ammonium hydroxide and the elements of sodium oxide, an oxide of aluminum or gallium, an oxide of silica, and having a composition, in terms of mole ratios of oxides, falling within the following ranges:

TABLE I

| | Broad | Preferred | Particularly Preferred |
|---|---|---|---|
| OH—/SiO$_2$ | 0.07–1.0 | 0.1–0.8 | 0.2–0.75 |
| R$_4$N+/(R$_4$N+ + Na+) | 0.2–0.95 | 0.3–0.9 | 0.4–0.9 |
| H$_2$O/OH— | 10–300 | 10–300 | 10–300 |
| SiO$_2$/Al$_2$O$_3$ | 5–120 | 20–110 | 70–100 | wherein R is propyl. This mixture is maintained at reaction conditions until the crystals of the zeolite are formed. Thereafter, the crystals are separated from the liquid and recovered. Typical reaction conditions consist of a temperature of from about 160° F. to 400° F. for a period of about 2 days to 60 days. A more preferred temperature range is from about 190° F. to 235° F., with the amount of time at a temperature in such range being from about 7 days to 21 days.

The digestion of the gel particles is carried out until crystals form. The solid product is separated from the reaction medium, as by cooling the whole to room temperature, filtering and water washing.

ZSM-5 is preferably formed as an aluminosilicate. The composition can be prepared utilizing materials which supply the elements of the appropriate oxide. Such compositions include aluminosilicate, sodium aluminate, alumina, sodium silicate, silica hydrosil, silica gel, silicic acid, sodium hydroxide and tetrapropylammonium hydroxide. Each oxide component utilized in the reaction mixture for preparing a member of the ZSM-5 family can be supplied by one or more initial reactants. For example, sodium oxide can be supplied by an aqueous solution of sodium hydroxide, or by an aqueous solution of sodium silicate. The reaction mixture can be prepared either batchwise or continuously. Crystal size and crystallization time of the ZSM-5 composition will vary with the nature of the reaction mixture employed. The zeolite contains tetrapropylammonium cations which are removed by calcination producing the H—Na form of the zeolite.

The zeolites used in the instant invention may have a certain proportion of the original cations associated therewith replaced by other cations. Exchange techniques known in the art may be used. Preferred replacing cations include ammonium and metal cations, including mixtures of the same. Preferably, the replacing cation is ammonium, and preferably the ammonium is converted to hydrogen by driving off ammonia to result in the replacing cation being hydrogen. Thus, as stated above preferably the ZSM-5 used to form the catalyst used in the present invention is predominantly in the hydrogen form.

By predominantly in the hydrogen form, we mean that a dominant characteristic of the ZSM-5 used to form the catalyst is that the ZSM-5 is in an acidic form as opposed to a basic form. A basic form is one where the ZSM-5 has substantial amounts of the original sodium; that is, the sodium that is present in the as-synthesized ZSM-5. Accordingly, preferably at least 80% of the sodium ions in the ZSM-5 used to form the catalyst have been replaced by hydrogen ions, more preferably at least 90%, still more preferably at least 95%, and most preferably at least 98% of the sodium ions have been replaced by hydrogen ions.

In accordance with these percentage removals, the amount of sodium left in the ZSM-5 will depend on the original amount present, which in turn will depend on factors such as the silica to alumina ratio. Keeping these qualifications in mind, ranges for sodium left in the ZSM-5 after it has been converted to the hydrogen form preferably are less than 0.1 wt. % of the original sodium, more preferably less than 0.06 wt. %, and most preferably less than 0.03 wt. %.

Typical ion exchange techniques include contacting the zeolite with a salt of a replacing cation or cations. Although a wide variety of salts can be employed, particular preference is given to chlorides, nitrates and sulfates.

In the process of the present invention, it is preferred to use the zeolite in a "bound" form, that is, with a refractory oxide as a binder for the overall catalyst particle. Suitable refractory oxide binders are alumina, silica, titania, clay, or mixtures thereof. This binder serves to hold the crystalline zeolite particles together in a catalyst particle of suitable size and suitable attrition resistance upon handling and use in the isomerization process. The amount of binder used versus zeolite is preferably between 10 and 65 percent binder by weight, more preferably between 20 and 50 percent binder.

Alumina is a particularly effective binder for the catalyst used in the ethylbenzene hydrodealkylation/isomerization process of the present invention. A preferred form of the alumina is that commonly referred to as Catapal-B, available from Condea-Vista Company.

A typical catalyst is in the form of a ¹⁄₁₆-inch diameter by ³⁄₁₆-inch length extrudate. Use of the zeolite powdered catalyst as prepared would result in too high a pressure drop in the preferred fixed bed used in the ethylbenzene hydrodealkylation/isomerization process.

The added hydrogenation metal, such as the preferred platinum, palladium, or nickel used in the catalyst, may be added to the catalyst by impregnation or ion exchange using known techniques. In general, the metals are added as salts, preferably of thermally decomposable anions such as the nitrate, nitrite, acetate, etc., or soluble metal complexes, by filling the pores of the catalyst with a solution of appropriate concentration to achieve the desired metal loading, equilibrating, drying and calcining to remove solvent, impurities and to decompose the salts to remove the volatile products. Alternatively, adsorption or other techniques well known in the art for introducing metals into porous substances may also be used.

BRIEF DESCRIPTION OF THE DRAWINGS

FIG. 2 is a graph illustrating the stability of PXATE for various ZSM-5 catalysts.

DETAILED DESCRIPTION OF THE DRAWINGS

Figure 1:
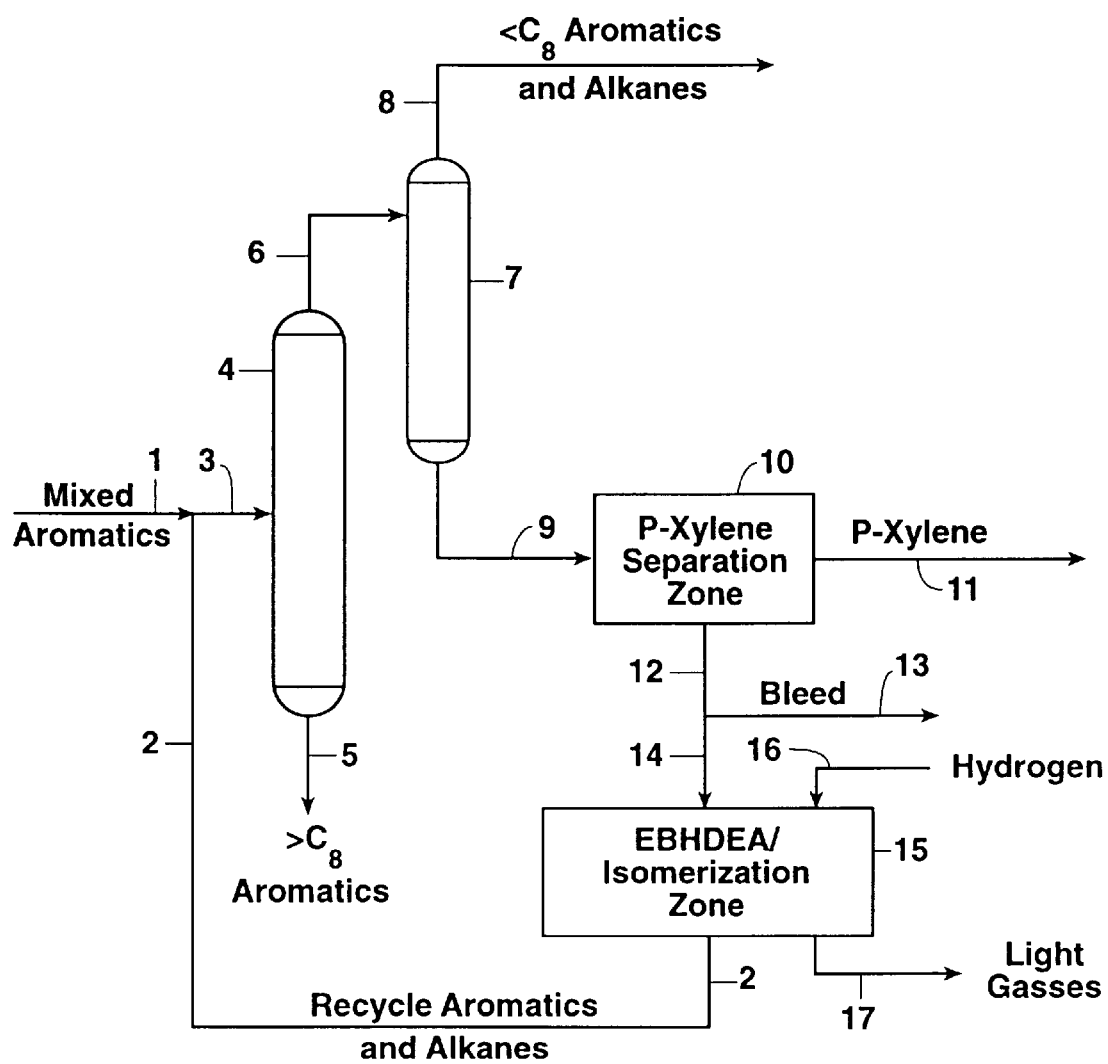
FIG. 1 is a schematic flow diagram illustrating the positioning of the ethylbenzene hydrodealkylation/isomerization reaction zone in a process sequence directed to producing paraxylene.

Referring now in more detail to FIG. 1, a mixed aromatic/paraffin feed in line 1 is combined with the line 2 effluent stream from ethylbenzene hydrodealkylation/isomerization zone 15. The combined streams are fed via line 3 to column 4 for distillation. The higher boiling aromatics—those having more than 8 carbon atoms—are taken as a bottoms fraction in line 5; the overhead comprising $C_8$ aromatics and lighter components is charged via a line 6 to another distillation unit column 7. In this second distillation column, the lower boiling aromatics—those having less than 8 carbon atoms—and any paraffinic components, are taken overhead in line 8. The bottoms from the second distillation, comprising $C_8$ aromatics, are then fed via line 9 to paraxylene separation zone 10.

In separation zone 10, about 25 to 95 percent of the paraxylene is removed by crystallization or by extraction. The crystallization can be carried out by low temperature processes, and extraction can be carried out by various processes, for example, the UOP "Parex Process" or the IFP "Eluxyl Process". Separated paraxylene is withdrawn via line 11 from zone 10.

The effluent (mother liquor) from the separation zone 10 is withdrawn via line 12 and is fed to ethylbenzene hydrodealkylation/xylene isomerization zone 15 which uses reaction conditions according to the present invention, as described above.

Provision is made via line 13 to bleed some of the paraxylene plant mother liquor as desired.

Gaseous hydrogen is fed into the ethylbenzene hydrodealkylation/xylene isomerization zone 15 via line 16. In accordance with a preferred embodiment of the present invention, only once-through hydrogen is used. Light gasses are removed from the ethylbenzene hydrodealkylation/isomerization zone 15 via line 17.

Finally, the ethylbenzene depleted, xylene isomerized stream from the ethylbenzene hydrodealkylation/xylene isomerization zone 15 is withdrawn via line 2 and is recycled to be combined with the incoming fresh feed.

Fresh feed to the process of the present invention preferably contains about 2 to 20 weight percent, preferably 5 to 20 weight percent, ethylbenzene based on $C_8$ aromatics. When operating this process in a continuous manner, the quantity of recycled $C_8$ aromatics is from 2 to 4 times that of the fresh feed; and the ethylbenzene in the feed to the paraxylene plant levels out at about 5 to 25 percent.

FIG. 2 is a graph of stability of PXATE for the ZSM-5 catalysts as discussed in the examples. The graph illustrates that the Pt ZSM-5 catalyst and process of the present invention maintains a stable PXATE while the comparative catalysts that contain magnesium show a declining PXATE.

Measurement of ZSM-5 Crystal Size by SEM

The method used is based on scanning electron microscopy (SEM). SEM is a common analytical technique for examining the morphology of materials at high magnifications. The range of magnifications for a common SEM instrument is typically 20× to 50,000×.

I. Specimen Preparation

For the purpose of this specification, the SEM sample was prepared by mounting a small amount of the zeolite powder onto an SEM specimen stub. The description of the procedure can be found in many standard microscopy text books. The procedure used to determine all of the crystal sizes given herein was as follows:

Step 1. A double sided sticky carbon tape, available from microscopy supplies vendors, was affixed to the specimen stub.

Step 2. A small amount of zeolite powder was spread onto the carbon tape using a stainless steel spatula.

Step 3. The excess zeolite powder was gently blown off using an air hose or a compressed air duster.

Step 4. A Pd—Au alloy film (approximately 15 nm thick) was sputtered onto the sample to prevent the sample from charging under the electron beam.

Note that (a) a representative portion of the powder was selected from the sample container, and (b) the mounting procedure was such that individual particles would be reasonably evenly spread out across the field of view at 10,000× magnification.

II. SEM Imaging

Step 1. The sample was surveyed at low magnifications, e.g., 500×–1000×, to look for representative areas to photograph.

Step 2. At least four representative images were recorded at the 10,000× magnification.

Step 3. The number of images recorded contained at least 200 zeolite crystals in total.

III. Image Analysis to Obtain Number Average Crystal Size

The analysis was performed on the SEM images of 10,000× magnification. The raw data was stored in a computer spreadsheet program, e.g., Microsoft Excel, Lotus 123, etc. The objective was to obtain the arithmetic mean crystal size ($d_{av}$) and its standard deviation ($\sigma$), where, The arithmetic mean $$d_{av} = (\Sigma n_i d_i)/(\Sigma n_i)$$

The standard deviation $$\sigma = (d_i - d_{av})^2/(\Sigma n_i))^{1/2}$$

Step 1. The recorded SEM image at 10,000× was scanned using a horizontal straight edge.

Step 2. The longest dimension of the individual crystals parallel to the horizontal line of the straight edge was measured and recorded. Those particles that were clearly large polycrystalline aggregates were not included in the measurement.

Step 3. 200 crystals were measured.

Step 4. The arithmetic mean ($d_{av}$) and the standard deviation ($\sigma$) were reported.

The results were cross-checked by transmission electron microscopy (TEM) to assure that the crystals measured in the SEM images were actually single crystals rather than polycrystalline aggregates.

When referring to crystal size for the ZSM-5 component of the catalyst of the present invention, we mean crystal size as determined in accordance with this procedure.

When an extrudate sample was examined and the starting zeolite powder was not available, the method was altered slightly. The well sampled extrudate was ground up in a mortar and pestel (not so severely as to cause loss of crystallinity of the zeolite phase) and the SEM analysis was performed on the resulting powder. Only those particles of the ground powder were included in the analysis which could be judged to be zeolitic material from the microscopist's observations of the crystalline habit (straight edges, non agglomerated binder and zeolite particles, etc.). This was still cross checked by TEM where in this case the sample was prepared by microtoming (or thin sectioning) and again where only those particles that could be judged clearly to be zeolitic particles were included in the measurement of the averages. Good agreement was observed between the two methods.

EXAMPLES

The hydrocarbon feeds used in all of the process examples below were feeds obtained from a commercial low pressure isomerization process. The composition of the feeds is given in the table below and was determined by gas chromatographic analysis.

TABLE II

Feed Composition

| Component, wt % | Feed I | Feed II |
|---|---|---|
| Non-aromatics-1 | 3.45 | 1.79 |
| Benzene | — | — |
| Nonaromatics-2 | 1.70 | 0.89 |
| Toluene | 1.05 | 0.76 |
| EB | 6.28 | 7.18 |
| PX | 9.69 | 10.83 |
| MX | 52.28 | 52.42 |
| OX | 24.20 | 23.92 |
| C9+ Aromatics | 1.35 | 2.21 |
| Total | 100.00 | 100.00 |
| Normalized Xylene Distribution - wt % | | |
| PX | 11.25 | 12.42 |
| MX | 60.67 | 60.14 |
| OX | 20.08 | 27.44 |
| Average Molecular Weight | 106.9 | 106.8 |
| Specific Gravity | 0.8669 | 0.8696 |

Examples 1, 2, 3 and 4 that follow describe preparation of catalysts, including preferred catalysts for use in the process of the present invention. All of these catalysts were made using a ZSM-5 zeolite, particularly an HZSM-5. The "H" connotes that the ZSM-5 is in predominantly the hydrogen form. The HZSM-5 we used was purchased from manufacturers of this zeolitic material. The following table lists the HZSM-5 manufacturers and gives the crystal size of the ZSM-5.

The crystal size measurements were made using a Scanning Electron Microscope (SEM). The number averaging method described in the section above entitled *Measurement of ZSM-5 Crystal Size by SEM* was used to determine the average crystal size of the ZSM-5 crystals that were used to make the catalysts.

BRIEF DESCRIPTION OF ZEOLITE SAMPLES

| Supplier | ID # | Form | Cation | Binder Amount | Crystal Size | Silica to Alumina Ratio |
|---|---|---|---|---|---|---|
| PQ | CBV 8020 | Powder | H | None | 0.7 micron | 80 |
| PQ | CBV 8062 | Extrudate | H | 20% | 0.54 micron | 80 |

Example 1

Preparation of Mg—Pt/ZSM-5 Catalyst

A catalyst designed to contain 1.9% Mg and 0.08% Pt on CBV 8062 was prepared according to the following procedure. 325.4 grams of CBV 8062 (300 grams of volatile-free extrudates) was weighed out. 62.6 grams of magnesium nitrate hexahydrate, Baker (assay 99.1%), was dissolved in deionized water. The magnesium nitrate solution was diluted to a volume of 115 milliliters which was calculated to be 100% of the total pore volume. The bound H-ZSM-5 was impregnated with the solution of magnesium nitrate by the method of incipient wetness. The solution was added by spraying during a fifteen-minute mixing period. The impregnated sample was allowed to soak for one hour, then dried for one hour at 127° C., and calcined in a preheated furnace at 500° C. for one hour in flowing air. The resulting sample was sized to an L/D=2 prior to the next impregnation step.

143 grams (140 grams volatile-free) Mg/CBV 8062 from the preceding impregnation was weighed out into a round bottomed flask. 0.7318 grams of platinum tetraammine dichloride from Johnson Matthey (assay 54.2% Pt) was dissolved with deionized water to a total volume of 57.3 milliliters, which was calculated to be about 102% of the total pore volume. The solution was used to impregnate the extrudates using the method of vacuum pore filling. During the solution addition, the mass was well shaken. Following the vacuum pore fill step, the mixture was allowed to soak for six hours and stirred each one-half hour for the first three hours of the soak. The moist catalyst was transferred to an evaporating dish. There was no excess liquid. It was dried for one hour at 127° C. It was then placed into a preheated furnace and calcined in flowing air for one hour at 288° C.

A microprobe analysis of the catalyst showed a non-uniform platinum distribution. All of the detectable platinum was found in a shell with a steep concentration slope beginning at the outer edge of the extrudate. No platinum was detected beyond about 20% of the distance from the edge to the center of the cross-sectioned cylinder.

Example 2

Preparation of Mg—Pt/ZSM-5 Catalyst

A catalyst designed to contain 1.5% Mg and 0.25% Pt on CBV 8062 was prepared according to the following procedure. 371.9 grams of CBV 8062 (350 grams of volatile-free extrudates) was weighed out. 57.3 grams of magnesium nitrate hexahydrate, EM Science (assay 99%), was dissolved in deionized water. The magnesium nitrate solution was diluted to a volume of 135 milliliters which was calculated to be 100% of the total pore volume. The bound H-ZSM-5 was impregnated with the solution of magnesium nitrate by the method of incipient wetness. The solution was added by spraying during a fifteen-minute mixing period. The impregnated sample was allowed to soak for one hour, then dried for one hour at 127° C., and calcined in a preheated furnace at 500° C. for one hour in flowing air. The resulting sample was sized to an L/D=2 prior to the next impregnation step.

153 grams (150 grams volatile-free) Mg/CBV 8062 from the preceding impregnation was weighed out into a round bottomed flask. 6.8 grams of 70% $HNO_3$ was added to 50 milliliters of deionized water. The pH was adjusted to about 9.05 by adding 40 drops of concentrated ammonium hydroxide. 0.686 grams of platinum tetraammine dichloride from Johnson Matthey (assay 54.7% Pt) was dissolved into the solution and water was added to a total volume of 63.7 milliliters, which was calculated to be about 102% of the total pore volume. pH of the solution was 9.51. The solution was used to impregnate the extrudates using the method of vacuum pore filling. During the solution addition, the mass was well shaken. Following the vacuum pore fill step, the mixture was allowed to soak for six hours and stirred each one-half hour for the first three hours of the soak. The moist catalyst was transferred to an evaporating dish. There was no excess liquid. It was dried for one hour at 149° C. It was then placed into a preheated furnace and calcined in flowing air for 30 minutes at 288° C.

A microprobe analysis of the catalyst showed a uniform platinum distribution across the cross-section of the extrudates.

Example 3

Preparation of Mg-Pt/ZSM-5 Catalyst

The procedure of Example 2 was followed to prepare a catalyst designed to contain 0.75% Mg and 0.25% Pt on CBV 8062. The pH of the buffered platinum tetraammine dichloride impregnation solution was 9.76.

A microprobe analysis of the catalyst showed a uniform platinum distribution across the cross-section of the extrudates.

Example 4

Preparation of Pt/ZSM-5 Catalyst Using H-ZSM-5 Extrudate

A catalyst designed to contain 0.25% Pt on CBV 8062 was prepared according to the following procedure. 172.5 grams (160 grams volatile-free) CBV 8062 from PQ was weighed out into a round bottomed flask. 7.2 grams of 70% $HNO_3$ was added to 50 milliliters of deionized water. The pH was adjusted to 9.05 by adding 40 drops of concentrated ammonium hydroxide. 0.7318 grams of platinum tetraammine dichloride from Johnson Matthey (assay 54.69% Pt) was dissolved into the solution and water was added to a total volume of 62.4 milliliters, which was calculated to be about 102% of the total pore volume. pH of the solution was 9.12. The solution was used to impregnate the extrudates using the method of vacuum pore filling. During the solution addition, the mass was well shaken. Following the vacuum pore fill step, the mixture was allowed to soak for six hours and stirred each one-half hour for the first three hours of the soak. The moist catalyst was transferred to an evaporating dish. There was no excess liquid. It was dried for one hour at 149° C. It was then placed into a preheated furnace and calcined in flowing air for 30 minutes at 288° C.

A microprobe analysis of the catalyst showed a uniform platinum distribution across the cross-section of the extrudates.

The following table summarizes the catalysts that were prepared.

BRIEF DESCRIPTION OF CATALYST SAMPLES

| Example | % Mg | % Pt | Pt Distribution |
|---|---|---|---|
| 1 | 1.9 | 0.08 | Eggshell |
| 2 | 1.5 | 0.25 | Uniform |
| 3 | 0.75 | 0.25 | Uniform |
| 4 | 0 | 0.25 | Uniform |

Example 5

Prior Art Low Pressure Xylene Isomerization Example

Ten grams of ZSM-5 powder CBV 8020, 0.7 micron crystal size, were formed to particles of 20–40 mesh. 0.6 gm of the 20–40 mesh ZSM-5 particles were then mixed with alundum and charged to a 0.5-inch diameter reactor. After dehydrating the catalyst in an inert gas, namely, nitrogen, the nitrogen flow was discontinued and hydrocarbon feed was passed over the catalyst.

For this example, Feed I was used. The feed composition is shown in Table II, above. Operating conditions included a pressure of 25 psig and a WHSV of 8.8 $hr^{-1}$. The WHSV was based on the zeolite component of the catalyst.

The reactor effluent was sampled periodically by an in-line sampling system and analyzed by gas chromatography. The reactor temperature was adjusted to achieve a nominal ethylbenzene conversion of 30 wt. %. Results are shown in Table III below.

TABLE III

| | | |
|---|---|---|
| Time On Stream - Hours | 26.9 | 71.8 |
| $H_2$ Added | NO | NO |
| $H_2$/EB M/M | — | — |
| $H_2$/HC Feed M/M | — | — |
| Pressure, Psig | 25 | 25 |
| WHSV, $hr^{-1}$ | 8.8 | 8.8 |
| Time On-Stream - hr. | 26.9 | 71.8 |
| Temperature - ° F. Reactor | 636 | 666 |
| Effl. Comp. wt. % | | |
| Non Arom.-1 | 8.88 | 4.25 |
| Benzene | 1.02 | 1.24 |
| Non Arom.-2 | 1.11 | 1.34 |
| Toluene | 2.43 | 2.43 |
| EB | 4.39 | 4.32 |
| PX | 17.27 | 18.67 |
| MX | 42.16 | 44.28 |
| OX | 18.07 | 19.24 |
| $C_9$+ Aromatics | 4.68 | 4.26 |
| Total | 100.00 | 100.00 |
| EB Conv. wt. % | 30.6 | 31.7 |
| Xylene loss - wt. % | 10.1 | 4.7 |
| EB Conv/Xyl. Loss Ratio | 3.0 | 6.8 |
| PX Approach To Eq. - % Xylene | 88.0 | 92.0 |

TABLE III-continued

| Distribution - wt. % | | |
|---|---|---|
| PX | 22.29 | 22.71 |
| MX | 54.4 | 53.88 |
| OX | 23.31 | 23.41 |
| PX Conc. At Eq. - wt. % | 23.76 | 23.70 |
| Fouling Rate - ° F./hr | | 1.5 |

Two operating periods are shown, 26.9 and 71.8 hours on-stream (HOS), at a temperature of 636° F. and 666° F., respectively. Note that the ethylbenzene (EB) conversion varied from 30.6 to 31.7 wt. %, and the xylene loss varied from 10.1 to 4.7 wt. %. This is a high xylene loss and results in an ethylbenzene conversion/xylene loss ratio which varied from 3.0 to 6.8. In addition, the paraxylene approach to equilibrium varied from 88–92%. In other words, the xylene isomerization was not complete, as an equilibrium concentration of paraxylene was not reached. Indeed, at 71.8 HOS, the paraxylene concentration on a xylene basis is 22.71 versus the equilibrium value of 23.70 wt. %. Furthermore, note that the reactor temperature had to be increased at the rate of 1.5° F./hr in order to hold an ethylbenzene conversion of ~30 wt. %.

Example 6

Test of 0.08% Pt/1.9% Mg/ZSM-5

The catalyst as prepared in Example 1 which contains 0.08% Pt and 1.9% Mg on CBV 8062 was tested as described in Example 5 above but with some minor modifications to the procedure, as described below, due to the presence of a hydrogenation component and the use of hydrogen. The objective of this test was to demonstrate the capability of a Pt/Mg/ZSM-5 catalyst to hydrodealkylate ethylbenzene to benzene and ethane and to do so with lower xylene losses than the prior art low pressure process at the same EB conversion. These goals are to be achieved while operating at low total system pressure and in particular at a low hydrogen partial pressure. A further objective was to determine the xylene isomerization stability of this catalyst by following how the Paraxylene Approach To Equilibrium (PXATE) behaved with time. The activity of a catalyst to isomerize xylenes to equilibrium at any point in time is determined by the degree to which the paraxylene (PX) concentration on a xylene basis approaches the equilibrium value. This measure is known as the Paraxylene Approach To Equilibrium or PXATE and is defined as follows:

$$PXATE = \frac{(PX_{prd} - PX_{fd}) * 100}{(PX_{eq} - PX_{fd})}$$

Where $PX_{prd}$ and $PX_{fd}$ is the concentration of PX in the product and the feed, respectively, on a xylene basis. Similarly, $PX_{eq}$ is the concentration of PX on a xylene basis at equilibrium. Thus if a xylene stream containing PX is isomerized such that the PX concentration in the product is the same as the PX concentration at equilibrium, then the PXATE is 100%.

Since the catalyst of Example 1 is a bound extrudate, and contains 80% of the ZSM-5 zeolite and 20% of an alumina binder, 0.75 grams sized to a particle size of 14–28 mesh, was charged to the reactor. This 0.75 gram charge equates to 0.6 gm of zeolite and is equivalent to the quantity of zeolite charged to the reactor in Example 5. In addition, following the catalyst dehydration step as in Example 5, the catalyst of this example was also treated in hydrogen at 950 F. for one hour. Operating conditions in the reactor included a pressure of 35 psig and a WHSV of 8.8 hr−1 based on the zeolite content of the catalyst or 7.0 hr−1 based on the extrudate charged. Hydrogen was added to the reactor on a once-through basis at a rate equivalent to a $H_2$/ethylbenzene (EB) mole ratio of 1.2/1. This is equivalent to a $H_2$/hydrocarbon feed mole ratio of 0.086. The EB conversion target was 50%. Following the treatment with hydrogen, the temperature was reduced to 675 F. and the feed introduced. The temperature was then increased until an EB conversion of 50% was attained. It should also be noted that the crystal size of the ZSM-5 zeolite contained in CBV 8062 is 0.54 microns. The feed used in this example was Feed II with the composition as shown in Table II. The catalyst was tested for a total of 671 hours. Results are shown in the Table below as a function of time on stream and in FIG. 2.

| Hours On Stream | 49.5 | 199.1 | 551.6 | 608.0 |
|---|---|---|---|---|
| Temperature - F. | 710 | 731 | 803 | 805 |
| EB Conversion - wt % | 49.95 | 50.55 | 53.85 | 52.29 |
| Xylene Loss - wt % | 3.00 | 2.80 | 2.56 | 2.18 |
| EBC/XYLLR | 16.67 | 18.07 | 21.06 | 24.03 |
| PXATE - % | 106.2 | 104.9 | 100.4 | 97.5 |

EBC/XYLLR = EB Conversion/Xylene Loss Ratio

The results show that a much higher EB conversion is achieved with the catalyst of Example 6 than the prior art catalyst and low pressure process of Example 5. In addition the xylene losses to achieve a given EB conversion are lower for the catalyst of Example 6 than the prior art catalyst. For this example where the nominal EB conversion was 50%, the xylene losses varied from 2.18 to 3.00% compared to 4.7 to 10.1% for the prior art catalyst where the nominal EB conversion was 30%. This better xylene selectivity is shown by a higher EB conversion/xylene loss ratio (EBC/XYLLR) which for the catalyst of this example varied from 16.67 to 24.03 compared to the prior art catalyst where the EBC/XYLLR varied from 3.0 to 6.8. Note that the lower the ratio for a given EB conversion, the higher the xylene losses and thus the lower the xylene selectivity. Furthermore, the reactor temperature was increased at the rate of 0.17 F./hr to maintain 50% EB conversion. This is an order of magnitude better than the prior art catalyst where the temperature was increased at the rate of 1.5 F./hr to maintain 30% EB conversion. However a drawback of the catalyst of Example 6, is the steady decline in the PXATE. After 608 hours on stream (HOS), the PXATE, which measures xylene isomerization activity, declined from 106.2% at the beginning of the run to 97.5%, indicating that at that point, an equilibrium PX concentration could not be reached. This represents an average rate of decline in the PXATE of 0.0157%/hr or 0.3768%/day. From a commercial standpoint this is not an acceptable decay rate in the PXATE.

Example 7

Test of 0.25% Pt/1.5% Mg/ZSM-5

The catalyst as prepared in Example 2 was tested as described in Example 6 using Feed II. This catalyst contained about 22% less magnesium than the catalyst used in Example 6. In addition the platinum content was higher. This catalyst was tested for a total of 695.5 hours.

Results are shown in the Table below and in FIG. 2.

| Hours On Stream | 47.5 | 198.7 | 551.4 | 600.0 | 695.5 |
|---|---|---|---|---|---|
| Temperature - F. | 702 | 716 | 767 | 774 | 789 |
| EB Conversion - wt % | 51.29 | 51.4 | 49.76 | 50.91 | 49.53 |
| Xylene Loss - wt % | 3.15 | 2.86 | 3.19 | 2.56 | 1.64 |
| EBC/XYLLR | 16.27 | 17.98 | 15.62 | 19.85 | 30.19 |
| PXATE - % | 104.84 | 103.82 | 100.68 | 98.84 | 96.31 |

EBC/XYLLR = EB Conversion/Xylene Loss Ratio

The results are very similar to those obtained in Example 6. The xylene losses are substantially lower than the prior art catalyst and process of Example 5, varying from 1.64 to 3.15% at a nominal EB conversion of 50%. This results in an EBC/XYLLR which varies from 15.62 to 30.19. In addition the initial temperature required to achieve 50% EB conversion is slightly lower than that in Example 6, namely 702 F. versus 710 F. Thus the catalyst of this example has a better initial EB conversion activity than the catalyst of Example 6. Furthermore, the reactor temperature was increased at the rate of 0.14 F./hr to maintain 50% EB conversion. This is an order of magnitude better than the prior art catalyst where the temperature was increased at the rate of 1.5 F./hr to maintain 30% EB conversion. However, just as for the catalyst in Example 6, the PXATE, which measures xylene isomerization activity, declines with time on stream. The PXATE declined from a value of 104.84% at the beginning of the run to 96.31% after 695.5 hours on stream, the end of the run. This represents an average rate of decline in the PXATE of 0.0132%/hr or 0.3159%/day. While this is a 16% lower decay rate in the PXATE than for the catalyst of Example 6, from a commercial standpoint this is not an acceptable decay rate in the PXATE.

Example 8

Test of 0.25% Pt/0.75% Mg/ZSM-5

The catalyst as prepared in Example 3 was tested as described in Example 6 using Feed II. This catalyst contained about 60% less magnesium than the catalyst used in Example 6 and 50% less than the catalyst used in Example 7. The platinum content was the same as the catalyst used in Example 7, namely, 0.25%. This catalyst was tested for a total of 756.0 hours.

Results are shown in the Table below and in FIG. 2.

| Hours On Stream | 51.8 | 195.7 | 539.7 | 651.9 | 756.0 |
|---|---|---|---|---|---|
| Temperature - degrees F. | 670 | 675 | 690 | 695 | 696 |
| EB Conversion - wt % | 52.93 | 50.85 | 51.67 | 52.37 | 50.79 |
| Xylene Loss - wt % | 3.94 | 1.67 | 2.13 | 3.73 | 2.95 |
| EBC/XYLLR | 13.43 | 30.49 | 24.26 | 14.03 | 17.2 |
| PXATE - % | 105.85 | 101.90 | 99.52 | 100.47 | 98.06 |

EBC/XYLLR = EB Conversion/Xylene Loss Ratio

The results are very similar to those obtained in Example 6. The xylene losses are substantially lower than the prior art catalyst and process of Example 5, varying from 1.67 to 3.94% at a nominal EB conversion of 50%. This results in an EBC/XYLLR which varies from 13.43 to 30.49. In addition, the initial temperature required to achieve 50% EB conversion is substantially lower than that in Example 6 and 7, namely 670 F. versus 710 F. for Example 6 and 702 F. for Example 7. Thus the catalyst of this example has an even better initial EB conversion activity than the catalyst of Example 7. Furthermore, the reactor temperature was increased at the rate of 0.03 F./hr to maintain 50% EB conversion. This is more than an order of magnitude better than the prior art catalyst where the temperature was increased at the rate of 1.5 F./hr to maintain 30% EB conversion. However, just as for the catalysts in Example 6 and 7, the PXATE, which measures xylene isomerization activity, declines with time on stream. In this example, the PXATE declined from a value of 105.85% at the beginning of the run to 98.06% after 756.0 hours on stream, the end of the run. This represents an average rate of decline in the PXATE of 0.0111%/hr or 0.2655%/day. This decay rate of 0.2655%/day represents a 30% reduction in the decay rate of the PXATE relative to the catalyst of Example 6, and 16% relative to the catalyst of Example 7. However, from a commercial standpoint this is still not an acceptable decay rate in the PXATE.

Example 9

Test of 0.25% Pt/ZSM-5

The catalyst as prepared in Example 4 was tested as described in Example 6 using Feed II. This catalyst contained NO magnesium but in all other respects is identical to the catalysts used in Examples 7 and 8 as it uses the same base, namely, CBV 8062 and has the same platinum content, namely, 0.25%. This catalyst was tested for a total of 812.3 hours. Results are shown in the Table below and in FIG. 2.

| Hours On Stream | 50.3 | 203.1 | 563.2 | 667.1 | 739.2 | 812.3 |
|---|---|---|---|---|---|---|
| Temperature - F. | 650 | 668 | 716 | 735 | 752 | 762 |
| EB Conversion - wt % | 48.06 | 47.51 | 47.91 | 50.04 | 48.60 | 45.73 |
| Xylene Loss - wt % | 4.22 | 2.51 | 2.82 | 2.60 | 2.43 | 2.56 |
| EBC/XYLLR | 11.40 | 18.94 | 17.00 | 19.22 | 20.01 | 17.83 |
| PXATE - % | 102.63 | 102.54 | 102.90 | 102.85 | 102.92 | 103.35 |

EBC/XYLLR = EB Conversion/Xylene Loss Ratio

From a xylene selectivity and EB conversion standpoint, the results are very similar to those obtained in Examples 6, 7 and 8. Thus xylene losses are substantially lower than the prior art catalyst and low pressure process of Example 5, varying from 2.43 to 4.22% at a nominal EB conversion of 50%. Furthermore, if the first xylene loss data point is ascribed to high initial catalyst activity and is rejected, then the subsequent xylene losses are more representative of the xylene losses for this example. In that case, the xylene losses varied from 2.43 to 2.82%. On this basis, the EBC/XYLLR varied from 17.83 to 20.11. This is still a substantial improvement over the prior art low pressure catalyst and process of Example 5, where the EBC/XYLLR varied from 3.0 to 6.8. This lower xylene loss and higher EBC/XYLLR is a surprising result for the catalyst of this Example. Indeed, we would have expected that the xylene losses with the catalyst of this Example would be similar to that of the prior art catalyst since the catalyst of this Example does not contain any magnesium and neither does the catalyst of the prior art low pressure process. Magnesium when added, tends to reduce catalyst acidity. Thus in both instances, i.e. Examples 5 and 9, we would expect the catalyst acidity to be the same, hence we would expect a similar level of xylene losses. Therefore, for the catalyst of this Example, and as in Example 5, we would have expected an EBC/XYLLR of 3.0 to 6.8. At 50% EB conversion, this translates to a xylene loss of from 7.35% to 16.66%. Surprisingly and as noted above, the xylene losses for the catalyst of this Example varied from 2.43% to 2.82%. An additional improvement is that the initial temperature required to achieve 50% EB conversion is substantially lower than that in Example 8, namely 650 F. versus 670 F. for Example 8. Thus the catalyst of this example has an even better initial EB conversion activity than the catalyst of Example 8 and could operate for a longer period of time than the catalysts of Example 6, 7 and 8. Indeed, the reactor temperature was increased at the rate of 0.15 F./hr to maintain 50% EB conversion. This is an order of magnitude better than the prior art catalyst where the temperature was increased at the rate of 1.5 F./hr to maintain 30% EB conversion. The order of magnitude lower fouling rate for the catalysts of Examples 6–9 is due to the presence of Pt in the catalysts. Pt in the presence of hydrogen, and surprisingly at low pressures, i.e. low hydrogen partial pressures, changes the mechanism of EB conversion from disproportionation as in Example 5, the prior art low pressure catalyst and process, to hydrodealkylation (to benzene and ethane) as in Examples 6–9.

Another significant improvement with this catalyst, which does not contain any magnesium, is that the PXATE does not decline with time on stream. Thus at the beginning of the run the PXATE was 102.63% and at the end of the run the PXATE was 103.35%, oscillating around 102.9% during the run. Thus the PXATE is very stable for the catalyst of this Example.

This means that a Pt/ZSM-5 catalyst which does not contain any magnesium, would maintain its full xylene isomerization activity, i.e. PXATE, for a substantially longer period of time than a Pt/Mg/ZSM-5 catalyst. Furthermore, a Pt/ZSM-5 catalyst still provides the benefits of a lower xylene loss-at a given EB conversion-and hence a higher EBC/XYLLR than the prior art low pressure catalyst and process. Also the Pt/ZSM-5 catalyst is comparable in its xylene losses and EBC/XYLLR, to the magnesium containing catalysts, i.e. Pt/Mg/ZSM-5. All in all the Pt/ZSM-5 is a better catalyst than the Pt/Mg/ZSM-5 and is commercially acceptable.

Comparative Example A

Comparison of Catalyst of the Present Invention to Catalyst Based on Large Crystal Size ZSM-5

The catalyst of the present invention which was prepared as in Example 4 and whose performance is described in Example 9, was compared to the performance of a platinum containing large crystal size ZSM-5. The performance of this platinum containing large crystal size ZSM-5 is described in U.S. Pat. No. 4,899,011, Example 1 and is identified as Catalyst A. The detailed results are shown in Table I in that reference and are summarized here for simplicity. Catalyst A is a ZSM-5 zeolite with a crystal size of approximately 2.5–4.0 microns. The catalyst contains 0.3% Pt and is a $\frac{1}{16}$ inch diameter extrudate which consists of 65 wt. % zeolite and 35 wt. % alumina binder. The extrudate catalyst has an alpha value of about 200 before Pt impregnation. Alpha value is a measure of catalyst acidity as described in U.S. Pat. No. 4,899,011. The high alpha value of 200 indicates that this is a highly acidic catalyst with a silica/alumina ratio of about 47. Catalyst A was tested at 200 PSIG and 800 F. The remaining operating conditions and the results are summarized in the following Table.

| Time On Stream-Hours | 3.5 | 9.5 | 16.0 |
|---|---|---|---|
| WHSV - hrs-1 | 2.9 | 8.6 | 8.7 |
| H$_2$/HC - Mole Ratio | 2.9 | 3.0 | 3.0 |
| EB Conversion - wt % | 99.6 | 99.6 | 99.0 |
| Xylene Loss - Wt % | 13.9 | 4.8 | 13.9 |
| EBC/XYLLR | 7.17 | 20.75 | 7.12 |
| PXATE - % | 62.7 | 49.4 | 54.0 |

EBC/XYLLR = EB Conversion/Xylene Loss Ratio

The first thing to note is that this highly acidic but large crystal size ZSM-5, Catalyst A, is a poor xylene isomerization catalyst on it's own and indeed has poor xylene isomerization activity. This is evidenced by the extremely low value of the PXATE, namely 54.0–62.7%. Note that it is substantially lower than the results obtained with any of the catalysts discussed in this invention and in particular the catalyst of this invention where the PXATE was consistently well above 100% during an 812 hour test as described in Example 9. In addition, Catalyst A, has the same deficiency, from the standpoint of a stable PXATE, as do the Pt/Mg/ZSM-5 catalysts described in Examples 6, 7 and 8. Note that for Catalyst A, the PXATE declines from an initial value of 62.7% (at 3.5 hours on stream) to 54.0% after 16.0 hours on stream. This represents a decline in the PXATE of 0.6960%/hr or 16.70%/day. Again, this decline rate is extremely high especially when compared to the catalyst of this invention, as described in Example 9, which in an extended test lasting 812 hours had an initial PXATE of 102.63% and showed no significant decline in the PXATE which was 103.35% at the end of the test.

Thus it is clear from this Comparative Example that for a low pressure EB Hydrodealkylation and Xylene Isomerization Process with a low H$_2$/EB mole ratio (thus very low H$_2$/HC feed mole ratio) and using hydrogen on a once-through basis, i.e. trickle hydrogen, a large crystal size ZSM-5 catalyst, such as Catalyst A is not preferred.

What is claimed is:

1. A process for the hydrodealkylation of ethylbenzene and the isomerization of xylenes, comprising contacting, in a reaction zone, a hydrocarbon feed containing ethylbenzene and xylenes, with a catalyst consisting of ZSM-5, and a Group VIII metal comprising platinum, wherein the paraxylene content of the xylenes in the feed is less than an equilibrium amount, the contacting is carried out in the presence of gaseous hydrogen, and the ZSM-5 has a crystal size of between 0.2 and 0.9 microns; at reaction zone conditions to hydrodealkylate ethylbenzene and isomerize xylenes to produce a reaction zone effluent comprising paraxylene and benzene; and wherein the reaction zone conditions comprise a reaction zone pressure below 125 psig and a hydrogen to ethylbenzene mole ratio of 0.3 to 15.

2. A process in accordance with claim 1 wherein the ZSM-5 crystal size is between 0.2 and 0.8 microns.

3. A process in accordance with claim 1 wherein the hydrogen to ethylbenzene mole ratio is between 1.0 and 11.

4. A process in accordance with claim 3 wherein the ZSM-5 has a silica to alumina ratio of between 10 and 300.

5. A process in accordance with claim 1 wherein reaction zone conditions comprise a temperature of 500° F. to 1000° F., a pressure of below 90 psig, a WHSV of 2 to 20, and a hydrogen to ethylbenzene feed mole ratio of 1.0 to 7.0.

6. A process in accordance with claim 5 wherein the ZSM-5 is predominantly in the hydrogen form.

7. A process in accordance with claim 1 wherein the feed comprises at least 70 wt. % $C_8$ aromatics.

8. A process in accordance with claim 4 wherein the catalyst contains 0.05 to 1.0 wt. % platinum, and the ZSM-5 crystal size is between 0.2 and 0.8 microns.

9. A process in accordance with claim 1 where the reaction zone pressure is 10 to 80 psig, the hydrogen to ethylbenzene mole ratio is between 1.0 and 7.0, the ZSM-5 crystal size is between 0.2 and 0.8 microns, the ethylbenzene content of the reaction zone effluent is no more than 50% the ethylbenzene content of the feed to the reaction zone, and the xylenes are isomerized in the reaction zone so that the paraxylene content of the reaction zone effluent is greater than 90% of its equilibrium value on a xylene basis.

10. A process in accordance with claim 9 wherein the reaction zone effluent has an ethylbenzene conversion to xylene loss ratio of greater than 15.

11. A process in accordance with claim 9 wherein the xylenes are isomerized in the reaction zone so that the paraxylene content is greater than 95% of its equilibrium value on a xylene basis.

12. A process in accordance with claim 9 wherein the hydrogen to ethylbenzene mole ratio is between 1.0 and 3.0.

13. A process in accordance with claim 9 wherein the ZSM-5 has a silica to alumina ratio is between 30 and 150.

14. A process in accordance with claim 1 wherein there is no recycle of hydrogen.

15. A process in accordance with claim 13 wherein the silica to alumina ratio is between 50 and 100.

16. A process in accordance with claim 14 wherein the process for the hydrodealkylation of ethylbenzene and the isomerization of xylenes is a commercial process.

17. A process in accordance with claim 14 wherein the hydrocarbon feed is contacted with the catalyst in the reaction zone at a rate of at least 500 bbl per day.

* * * * *